United States Patent
Tellier et al.

[11] 3,951,964
[45] Apr. 20, 1976

[54] METHOD FOR PREPARING AZINES

[75] Inventors: Pierre Tellier, Ouillins; Henri Mathais, Sainte Foy-les-Lyon; Jean-Pierre Schirmann, Brignais; Francis Weiss, Pierre-Benite, all of France

[73] Assignee: Produits Chimiques Ugine Kuhlmann, Saint-Denis, France

[22] Filed: Nov. 22, 1972

[21] Appl. No.: 308,836

[30] Foreign Application Priority Data
Nov. 23, 1971 France............................ 71.41867
Mar. 13, 1972 France............................ 72.08580

[52] U.S. Cl................... 260/240 G; 260/345.1; 260/345.9; 260/465 E; 260/465.5 R; 260/566 B
[51] Int. Cl.²...................................... C07C 119/00
[58] Field of Search......... 260/566 B, 240 G, 345.1, 260/345.9, 465 E, 566 B, 465.5 R

[56] References Cited
UNITED STATES PATENTS
2,870,206   1/1959   Meyer et al...................... 260/566 B

*Primary Examiner*—Gerald A. Schwartz
*Attorney, Agent, or Firm*—Pennie & Edmonds

[57] ABSTRACT

A method is disclosed for preparing symmetrical azines of the formulas

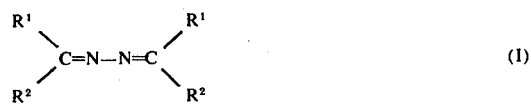
(I)

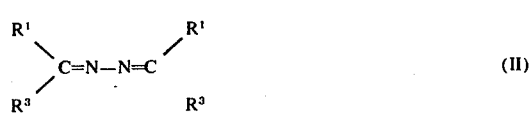

(II)

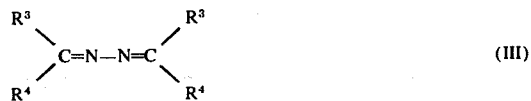

(III)

and unsymmetrical azines of the formulas

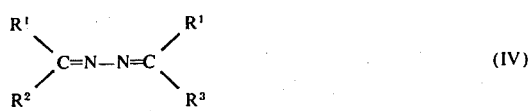
(IV)

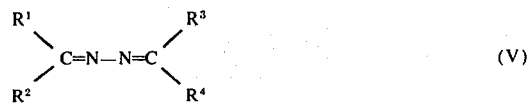

(V)

and mixtures of azines (I), (II) and (IV) and (I), (III) and (V), wherein $R^1$, $R^2$, $R^3$ and $R^4$ each is a hydrogen atom, a straight chain alkyl radical of from 1 to 12 carbon atoms, a branched chain alkyl radical or unsubstituted or alkyl substituted cycloalkyl radical of from 3 to 12 carbon atoms, a hydrocarbon radical of from 6 to 12 carbon atoms containing a benzene ring; further provided that $R^1$ and $R^2$ can be the same or different radicals, $R^3$ is a radical different from $R^1$ and $R^2$ and $R^3$ and $R^4$ are radicals different from each other and each are different from $R^1$ and $R^2$; or $R^1$ and $R^2$ or $R^1$ and $R^3$ or $R^3$ and $R^4$ bonded to the same carbon atom together form an unsubstituted or aliphatic substituted alkylene radical of from 3 to 11 carbon atoms, each of the aforesaid radicals being unsubstituted or substituted with one or more radicals which are stable in the medium in which the azines are produced.

The method comprises reacting ammonia and a carbonyl compound of the formula

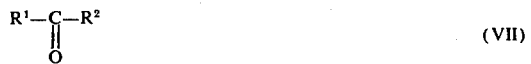
(VII)

alone or together with a different carbonyl compound

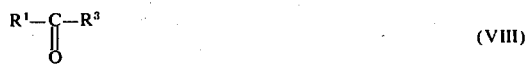
(VIII)

or
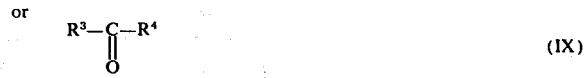
(IX)

wherein $R^1$, $R^2$, $R^3$ and $R^4$ each have the same meaning defined above with at least one diacyl peroxide (acyl peroxide) which are compounds having one or several groups of the structure

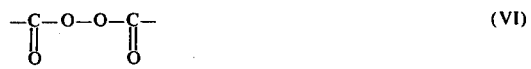
(VI)

and recovering the azine or mixture of azines from the reaction medium.

4 Claims, No Drawings

METHOD FOR PREPARING AZINES

BACKGROUND OF THE INVENTION

I. Field of the Invention

This invention relates to a method for preparing symmetrical azines as well as mixtures containing symmetrical and unsymmetrical azines.

II. Description of the Prior Art

Aldehydes are known to react with ammonia in a complex manner giving rise to various addition, condensation or polymerization products (see for example, *The Chemistry of the CarbonNitrogen Bond*, S. Patai, Interscience, London, 1967, page 67) which can react with hydrogen peroxide to form unstable peroxide products.

Moreover, it is known that ammonia, an aldehyde or ketone, and hydrogen peroxide react together to produce aminoperoxides (*J. Chem. Soc.* (C), 1969 page 2663) and in the presence of such catalysts as tungstic or molybdic acid, a mixture of cyclohexanone and ammonia is oxidized by hydrogen peroxide to form cyclohexanoneoxime (*J. Gen. Chem.* (U.S.S.R.), 1960, 30 1635), or in the presence of the ammonium salts or hydroxides of metals of Group Ia and IIa of the Periodic Table of the Elements, result in azines (see copending commonly assigned application Ser. No. 267,921, filed June 30, 1972).

One known method for preparing azines comprises oxidizing ammonia in the presence of a ketone or aldehyde by means of an oxidizing medium comprising hydrogen peroxide and cyanogen or a nitrile. This method is fully disclosed in commonly assigned pending U.S. application Ser. No. 752,413, filed June 11, 1971.

Another known method for preparing azines comprises oxidizing a secondary alcohol in the liquid phase to form peroxide products of the auto-oxidation of the alcohol and subsequently reacting the peroxidic products with ammonia in the presence of cyanogen or a nitrile. This method is fully disclosed in commonly assigned pending U.S. application Ser. No. 230,038, filed Feb. 28, 1972.

Still another known method for preparing azines comprises reacting a carbonyl compound, ammonia and a percarboxylic acid. This method is fully disclosed in commonly assigned U.S. application Ser. No. 290,507, filed Sept. 20, 1972.

Percarboxylic acids are also known to react with N-substituted imines in an anhydrous medium to give oxaziridines (German Pat. Nos. 952,895 and 959,094). It is also known that the decomposition of diacyl peroxides, largely used in the initiation of free-radical polymerization of ethylenic monomers, is greatly accelerated in the presence of amine compounds (see for example Dr. Swern, "Organic Peroxides," Vol. 1, Wiley-Interscience, New York, 1970 and the references cited in this work).

SUMMARY OF THE INVENTION

It has been surprisingly discovered that symmetrical azines of the formulas

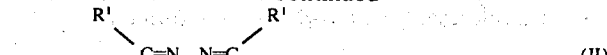

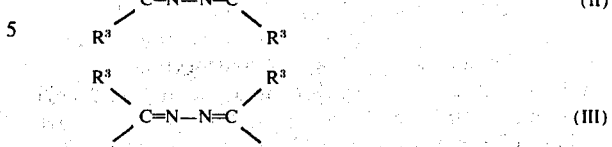

and unsymmetrical azines of the formulas

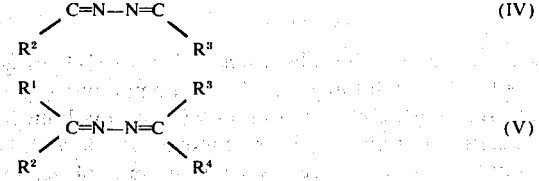

can be conveniently prepared in good yields by reacting ammonia and a carbonyl compound of the formula

alone or together with a different carbonyl compound

or

wherein $R^1$, $R^2$, $R^3$ and $R^4$ each have the same meaning defined above with at least one diacyl peroxide (acyl peroxide) which are compounds having one or several groups of the structure

and recovering the azine or mixture of azines from the reaction medium.

When a single carbonyl compound (VII) is reacted according to the method of this invention, a symmetrical azine having the formula

is produced.

When, for example, both $R^1$ and $R^2$ of carbonyl compound (VII) is hydrogen, the carbonyl compound is formaldehyde and the azine resulting from this method is the symmetrical aldazine, formaldazine, which has the formula

When only one of the substituents is hydrogen, the resulting aldazine, for example, has the formula $$R^1 - CH = N - N = CH - R^1$$

wherein the substituent $R^1$ is not hydrogen.

When neither of the substituents of the carbonyl compound (VII) is hydrogen, the carbonyl compound (VII) is a ketone and the resulting azine is a symmetrical ketazine of the formula

  (I)

wherein none of the substituents $R^1$ and $R^2$ is hydrogen.

When in addition to carbonyl compound (VII), a different carbonyl compound (VIII) is simultaneously reacted according to the method of this invention, a mixture of symmetrical and unsymmetrical azines of the formulas

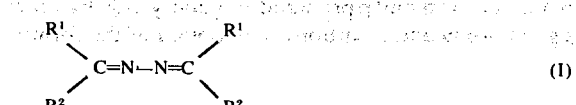  (I)

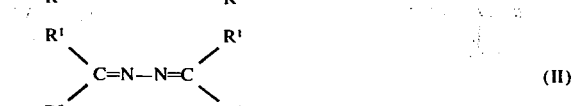  (II)

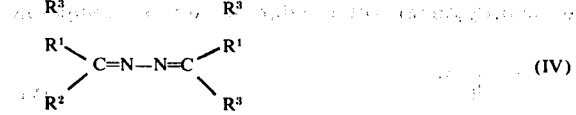  (IV)

is produced.

And if in addition to carbonyl compound (VII), a different carbonyl compound (IX) is simultaneously reacted according to the method of this invention, a mixture of symmetrical and unsymmetrical azines of the formulas

  (I)

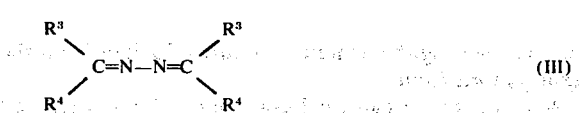  (III)

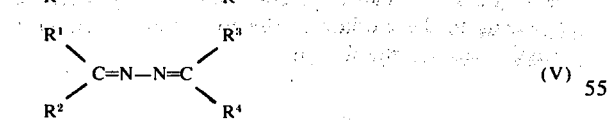  (V)

is produced.

When both carbonyl compounds (VII) and (VIII) or (VII) and (IX) are aldehydes, a mixture of symmetrical and unsymmetrical aldazines will be obtained. Similarly, if both carbonyl compounds (VII) and (VIII) or (VII) and (IX) are ketones, a mixture of symmetrical and unsymmetrical ketazines will be produced. And if one of the carbonyl compounds (VII), (VIII) or (IX) is an aldehyde and the other carbonyl compound which is being simultaneously reacted is a ketone, the method of this invention will yield a mixture of azines containing a symmetrical ketazine and an unsymmetrical azine possessing the characteristics of both an aldazine and a ketazine.

Any number of different aldehydes and/or ketones may be reacted according to the method of this invention to yield mixtures of azines, the number of which are present in the mixture being made to depend upon the number of carbonyl compounds reacted.

DETAILED DESCRIPTION OF THE INVENTION

The carbonyl compounds of this invention can contain ethylenic bonds and substituents which are stable in the reaction medium such as chlorine, bromine and fluorine atoms and nitro, hydroxy, alkoxy, carboxylic acid, carboxylic amide or ester and nitrile groups.

Some examples of aldehydes conforming to formulas (VII), (VIII) or (IX) which are advantageously employed in the process of this invention include formaldehyde, acetaldehyde, propionaldehyde, butyraldehyde, isobutyraldehyde, n-pentanal, pival aldehyde, oenanthal, 2-ethylhexanal, Δ-3 tetrahydrobenzaldehyde, hexahydrobenzaldehyde, 5-norbornene-2-carboxaldehyde, tetrahydropyran2 -carboxaldehyde, benzaldehyde, monochlorobenzaldehyde, p-nitrobenzaldehyde, anisaldehyde, β-chloropropionaldehyde, β-methoxypropionaldehyde, β-ethoxypropionaldehyde and 4-cyano-2, 2-dimethylbutyraldehyde.

Some examples of ketones conforming to formula (VII), (VIII) or (IX) which are advantageously employed in the process of this invention include acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyclooctanone, cyclodecanone and cyclododecanone.

Some examples of diacyl compounds having one or several structural groups

  (VI)

which are advantageously employed in the process of this invention include diacyl compounds of the formulas

  (VIa)

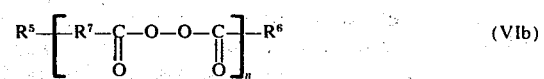  (VIb)

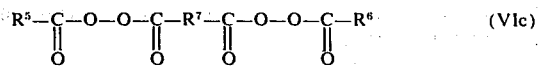  (VIc)

and

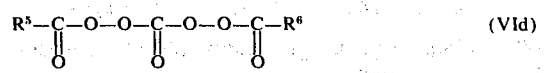  (VId)

wherein $n$ is 2 to 30, $R^5$ and $R^6$ each is a straight chain alkyl radical of from 1 to 18 carbon atoms, a branched chain alkyl radical or unsubstituted or substituted cycloalkyl radical of from 3 to 18 carbon atoms, a hydrocarbon radical of from 6 to 18 carbon atoms containing at least one aromatic nucleus, a radical containing at least one 5 or 6 membered heterocyclic oxygen or nitrogen-containing nucleus and having 4 to 18 carbon atoms, an alkoxy radical of 1 to 18 carbon atoms or $R_5$ and $R_6$ can together form an unsubstituted or aliphatic substituted 1,2-alkylene radical of 2 to 18 carbon atoms or a 1,2-arylene radical of 6 to 18 carbon atoms and $R^7$ is nothing or represents a linear divalent aliphatic radical of 2 to 10 carbon atoms, a branched or cyclic divalent aliphatic radical of 3 to 10 carbon atoms, an arylene or arylalkylene radical of 6 to 12 carbon atoms, each of the aforesaid radicals being unsubstituted or substituted with one or more radicals which are stable in the reaction medium such as chlorine, bromine and fluorine atoms and nitro, hydroxy, alkoxy, carboxylic acid, carboxylic amide or ester and nitrile groups.

Specific examples of diacyl peroxides conforming to formula (VIa) which have been found to be useful include the following acyl peroxides: monochloroacetyl, trifluoroacetyl, propionyl, β-chloropropionyl, β-methoxypropionyl, β-carboxypropionyl, n-butyryl, perfluoro-n-butyryl, isobutyryl, perfluoroisobutyryl, crotonyl, valeryl, isovaleryl, pivaloyl, hexanoyl, heptanoyl, octanoyl, 2-ethylhexanoyl, nonanoyl, decanoyl, lauroyl, myristoyl, palmitoyl, stearoyl, cyclohexanecarbonyl, norbornane-2-carbonyl, benzoyl, o-toluyl, m-chlorobenzoyl, p-chlorobenzoyl, 2,4-dichlorobenzoyl, p-methoxybenzoyl, p-nitrobenzoyl, m-trifluoromethylbenzoyl, p-phenylbenzoyl, o-carboxybenzoyl, α-naphthoyl, β-naphthoyl, 2-furoyl and nicotenoyl peroxides; the mixed peroxides such as acetyl and benzoyl, acetyl and butyryl, isobutyryl and benzoyl, acetyl and lauroyl and stearoyl and benzoyl peroxides.

Polymeric peroxides (VIb) and mixed peroxides (VIc) derived from the following diacids of the formula

HOOC — $R^7$ — COOH can advantageously be employed: oxalic (where $R^7$ is nothing), succinic (where $R^7$ is $-(CH_2)_2-$ ), glutaric (where $R^7$ is $-(CH_2)_3-$), adipic (where $R^7$ is $-(CH_2)_4-$), pimelic (where $R^7$ is $-(CH_2)_5-$), dodecanedioic (where $R^7$ is $-(CH_2)_{10}-$), cyclohexane-1,2-dicarboxylic or cyclohexane-1,4-dicarboxylic (where $R^7$ is  ), o-phthalic, isophthalic and terephthalic.

The peroxides (VIa) derived from carbonic acid in which at least one of the radicals $R^5$ or $R^6$ is an alkoxy group such as isopropoxycarbonyl and benzoyl, methoxycarbonyl and lauroyl, isopropoxycarbonyl and lauroyl, 3,3,5-trimethylcyclohexyloxycarbonyl and lauroyl peroxides, isopropyl peroxydicarbonate and cyclohexylperoxydicarbonate can advantageously be employed.

Some examples of the (VId) peroxides which can be used include the mixed dianhydrides of diperoxycarbonic acid and benzoic, caproic, lauric and 2-ethylhexanoic acids.

The reaction components are advantageously reacted in the liquid phase and mixed seriatim or as various combinations. For example, the reaction components can be separately or simultaneously introduced into the reactor on a continuous or batchwise basis. The diacyl peroxide can be added to a mixture of ammonia and the carbonyl compound or the ammonia or ammonia solution can be added to a mixture of the diacyl peroxide and the carbonyl compound. It is advantageous to employ a solvent or blend of solvents to maintain a homogenous reaction medium or provide at least a partial solubilization of the reaction components. Examples of solvents which can be used for this purpose include water and the saturated alcohols having 1 to 6 carbon atoms such as methanol, ethanol, n-propanol, isopropanol, n-butanol, 2-butanol, isobutanol, tert-butanol, the amyl alcohols and cyclohexanol. Non-polar solvents can also be used for solubilizing the diacyl peroxides which are insoluble or only slightly soluble in the polar reaction medium for example, the aliphatic, cycloaliphatic or aromatic hydrocarbons of up to 12 carbon atoms. Specific examples of such non-polar solvents include pentane, hexane, heptane, cyclohexane, benzene, toluene, the xylenes, halogenated solvents such as methylene chloride, chloroform, carbon tetrachloride, 1,2-dichloroethane, monochlorobenzene, nitrobenzene or blends of the aforesaid solvents. The overall reaction medium can be homogeneous or heterogenous and can consist of two non-miscible or partly miscible and/or one or several solid phases such as crystallized diacyl peroxide in the process of becoming dissolved or ammonium salts precipitating during the reaction. In order to obtain optimum results, it is necessary to provide sufficient agitation for the reaction medium, especially when the reaction medium is heterogenous.

The temperature of the reaction can advantageously be from about −20° to 100°C. The reaction can be carried out at or below atmospheric pressure or at a pressure of up to 10 atmospheres if such is necessary to maintain the ammonia in solution.

The reaction components can be employed in stoichiometric quantities but it is also possible to use other proportions in which case, it is advantageous to react up to about a 10-fold excess of ammonia and/or carbonyl compound by comparison to the amount of diacyl peroxide.

The calculation of the quantity of ammonia reacted should take into account that the carboxylic acids which are formed in the reaction (the amount depending upon the diacyl peroxide used) can be neutralized by an equivalent amount of base, advantageously ammonia. The quantity of ammonia needed to achieve neutralization can be reduced or eliminated if desired by previously adding to the reaction medium another base, as for example, a hydroxide or carbonate of an alkaline or alkaline earth metal.

It can be advantageous to add one or more known and conventional stabilizers for peroxidic compounds or substances which exercise a buffering action on the pH of the reaction medium. For example, from about 0.1 to 1.0% by weight of the reaction medium of phosphoric acid, citric acid, nitrilotriacetic acid, ethylenediaminetetraacetic acid or the alcaline metal or ammonium salts of the aforesaid acids can be used.

Upon completion of the reaction, the azines can be removed from the medium by means of known and conventional techniques including extraction with a non-miscible solvent, fractional distillation or a combination of these two methods.

The azines of this invention are useful as intermediates in the preparation of many important products and in particular are useful for preparing hydrazine and hydrazine salts of hydrolysis according to known and conventional methods. Hydrolysis of the azines releases the carbonyl compounds which can be recycled for preparing additional quantities of azines according to the method of this invention.

The following examples are illustrative of the method of this invention. Although the examples employ but a single carbonyl compound resulting in symmetrical azines it is understood that the same procedures can be followed except that two or more different aldehydes or ketones or one or more aldehydes and ketones are reacted to result in a mixture of symmetrical and unsymmetrical azines as hereinbefore described.

EXAMPLE 1

14.5 gm acetone (0.25 mole), 5 gm water, 40 gm methanol and 0.25 gm of the disodium salt of ethylenediaminetetraacetic (disodium EDTA) acid were added to a reactor and thereafter, 6.8 gm ammonia (0.4 mole) were dissolved in the medium. Following this, 24.2 gm benzoyl peroxide (0.1 mole) were introduced into the medium while the temperature was maintained at 20°C and the medium was left to react for 1 ¼ hr. at this temperature while gaseous ammonia at a rate of 1.7 gm (0.1 mole) per hour was bubbled therethrough. At the end of the reaction, the ammonium salt which had precipitated was filtered and the acetoneazine present in the solution was measured by chemical or vapor phase chromatographic (VPC) analysis. 8.8 gm acetoneazine (0.078 mole) corresponding to a yield of 78% by comparison to the peroxide used was formed.

EXAMPLE 2

Substantially the same conditions of EXAMPLE 1 were repeated with the exception that 38 gm of 2,4-dichlorobenzoyl peroxide (0.1 mole) were used instead of benzoyl peroxide. 7.2 gm acetoneazine (0.064 mole) corresponding to a yield of 64% by comparison to the peroxide used was formed.

EXAMPLE 3

Substantially the same conditions of EXAMPLE 1 were repeated with the exception that 39.8 gm of lauroyl peroxide (0.1 mole) were used instead of benzoyl peroxide and the medium was left to react for 4 ¼ hrs. at 20°C. 9.4 gm acetoneazine corresponding to a yield of 84% by comparison to the peroxide used was formed.

EXAMPLE 4

Substantially the same conditions of EXAMPLE 1 were repeated with the exception that 23.4 gm of succinyl monoperoxide or β-carboxypropionyl peroxide (0.1 mole) were used instead of benzoyl peroxide and the medium was left to react for 3 ½ hrs. at 20°C. 3.25 gm acetoneazine (0.029 mole) corresponding to a yield of 29% by comparison to the peroxide used was formed.

EXAMPLE 5

18gm methylethylketone (0.25 mole), 5 gm water, 50 gm methanol and 0.25 gm disodium EDTA were placed in a reactor, then 0.7 gm ammonia (0.41 mole) followed by 24.2 gm benzoyl peroxide (0.1 mole) were added to the medium, maintained at 20°C, over 12 minutes. After reacting at this temperature for an hour, the precipitated ammonium salt was filtered and the acetoneazine measured by chemical and VPC analysis. 9.3 gm (0.066 mole) acetoneazine corresponding to a yield of 66% by comparison to the peroxide used was formed.

EXAMPLE 6

EXAMPLE 5 was substantially repeated using 24.5 gm cyclohexanone (0.25 mole) in place of methylethylketone. 15.2 gm cyclohexanoneazine (0.079 mole) corresponding to a yield of 79% by comparison to the peroxide used was formed.

EXAMPLE 7

EXAMPLE 6 was substantially repeated replacing the benzoyl peroxide with 42.6 gm lauroyl peroxide (0.1 mole). 13.25 gm cyclohexanone azine (0.069 mole) corresponding to a yield of 69% by comparison to the peroxide used was formed.

EXAMPLE 8

14.5 gm acetone (0.25 mole), 5 gm water, 40 gm methanol and 0.25 gm of disodium EDTA were added to a reactor and 6.8 gm ammonia (0.4 mole) were then dissolved in the medium. 41.9 gm of a 75% mixture of nonanoyl peroxide (0.1 mole) of the formula

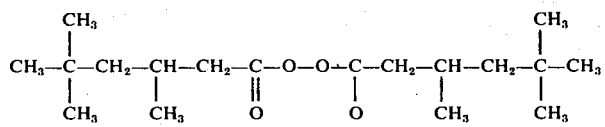

a product available from Societe Chalonnaise des Peroxydes Organiques were added to the reaction medium and the medium was left to react for 50 minutes at 20°C. At the end of the reaction, the precipitated ammonium salt was filtered and the acetoneazine present in the solution was measured by chemical and VPC analysis. 10.1 gm acetoneazine (0.090 mole) corresponding to a yield of 90% by comparison to the peroxide used was formed.

EXAMPLE 9

EXAMPLE 8 was substantially repeated with the exception that 89.6 gm of a 23% commercial solution of isopropyl peroxydicarbonate (0.1 mole) of the formula

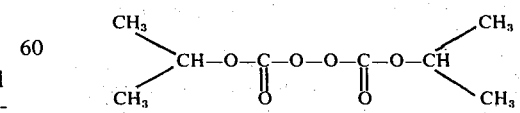

available from Societe Chalonnaise des Peroxydes Organiques was used in place of nonanoyl peroxide. After reacting for 1 ¼ hr. at 20°C, 6.9 gm acetoneazine (0.062 mole) corresponding to a yield of 62% by comparison to the peroxide used was formed.

EXAMPLE 10

EXAMPLE 8 was substantially repeated with the exception that 33.5 gm of an 85.4% mixture of cyclohexyl peroxydicarbonate (0.1 mole) of the formula

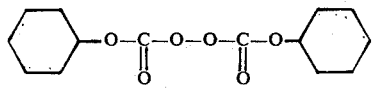

was used in place of nonanoyl peroxide. After reacting for ½ hr. at 20°C, 10.26 gm acetoneazine corresponding to a yield of 91.5% by comparison to the peroxide used was formed.

EXAMPLE 11

24.5 gm cyclohexanone (0.25 mole), 5 gm water, 40 gm methanol and 0.25 gm disodium EDTA were added to a reactor to which was then added 6.8 gm ammonia (0.4 mole). 44 gm of an 87% mixture of 2,4-dichlorobenzoyl peroxide (0.1 mole) were added to the reaction medium (a commercial product available from Societe Nourylande) and the medium was left to react for ¼ hr. at a temperature of 20°C. 18.25 gm of cyclohexanoneazine (0.095 mole) corresponding to a yield of 95% by comparison to the peroxide used was formed.

EXAMPLE 12

EXAMPLE 11 was substantially repeated except that 36.5 gm of a 74% mixture of succinyl monoperoxide (0.1 mole) were used in place of 2,4-dichlorobenzoyl peroxide. After reacting for ¼ hr. at 20°C, 10.56 gm of cyclohexanoneazine (0.55 mole) corresponding to a yield of 55% by comparison to the peroxide used was formed.

EXAMPLE 13

EXAMPLE 11 was substantially repeated except that 89.6 gm of a 23% commercial solution of isopropyl peroxydicarbonate (0.1 mole) were used in place of 2.4-dichlorobenzoyl peroxide. After ¼ hr. at 20°C, 12.5 gm of cyclohexanoneazine (0.065 mole) corresponding to a 65% yield by comparison to the peroxide used was formed.

EXAMPLE 14

EXAMPLE 11 was substantially repeated except that 33 gm of an 88% mixture of cyclohexyl peroxydicarbonate (0.1 mole) was used in place of 2,4-dichlorobenzoyl peroxide. After reacting for an hour at a temperature of 20°C, 14 gm of cyclohexanoneazine corresponding to a yield of 73% by comparison to the peroxide used was formed.

EXAMPLE 15

EXAMPLE 11 was substantially repeated using 42 gm of a 75% mixture of nonanoyl peroxide (0.1 mole) in place of 2,4-dichlorobenzoyl peroxide. After 4 hr. of reacting at 20°C, 12.1 gm of cyclohexanoneazine (0.063 mole) corresponding to a yield of 63% by comparison to the peroxide used was formed.

We claim:
1. A method for preparing azines which consists of reacting
   a. ammonia;
   b. a carbonyl compound selected from formaldehyde, acetaldehyde, propionaldehyde, butyraldehyde, isobutyraldehyde, n-pentanal, pival aldehyde, oenanthal, 2-ethylhexanal, Δ-3-tetrahydrobenzaldehyde, hexahydrobenzaldehyde, 5-norbornene-2-carboxaldehyde, tetrahydropyran-2-carboxaldehyde, benzaldehyde, monochlorobenzaldehyde, p-nitrobenzaldehyde, anisaldehyde, β-chloropropionaldehyde, β-methoxypropionaldehyde, β-ethoxypropionaldehyde, 4-cyano-2,2-dimethylbutyraldehyde, acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyclooctanone, cyclodecanone and cyclododecanone, and mixtures thereof;
   c. at least one diacyl peroxide selected from monochloroacetyl, trifluoroacetyl, propionyl, β-chloropropionyl, β-methoxypropionyl, β-carboxypropionyl, n-butyryl, perfluoro-n-butyryl, isobutyryl, perfluoroisobutyryl, crotonyl, valeryl, isovaleryl, pivaloyl, hexanoyl, heptanoyl, octanoyl, 2-ethylhexanoyl, nonanoyl, decanoyl, lauroyl, myristoyl, palmitoyl, stearoyl, cyclohexanecarbonyl, nonbornane2-carbonyl, benzoyl, o-toluyl, m-chlorobenzoyl, p-chlorobenzoyl, 2,4-dichlorobenzoyl, p-methoxybenzoyl, p-nitrobenzoyl, m-trifluoromethylbenzoyl, p-phenylbenzoyl, o-carboxybenzoyl, a naphthoyl, 2-furoyl and nicotenoyl peroxides; mixed acetyl and benzoyl, acetyl and butyryl, isobutyryl and benzoyl, acetyl and lauroyl and stearoyl and benzoyl peroxides; diacyl peroxides derived from oxalic, succinic, glutaric, adipic, pimelic, dodecanedioic, cyclohexane-1,2-dicarboxylic, cyclohexane-1,4-dicarboxylic, o-phthalic, isophthalic, and terephthalic acid; mixed isopropoxycarbonyl and benzoyl, methoxycarbonyl and lauroyl, isopropoxycarbonyl and lauroyl, 3,3,5-trimethylcyclohexyloxycarbonyl and lauroyl peroxides, isopropylperoxydicarbonate cyclohexyl-peroxydicarbonate peroxides; and mixed dianhydrides of diperoxycarbonic acid and benzoic, caproic, lauroic and 2-ethylhexanoic acids,
and recovering the azine or mixtures of azines from the reaction medium.

2. The method of claim 1 wherein the reaction is carried out in the presence of a solvent comprising a saturated alcohol of from 1 to 6 carbon atoms.

3. The method of claim 1 wherein the reaction is carried out at a temperature between about −20°C and 100°C.

4. The method of claim 1 wherein the molar ratios of carbonyl compound and/or ammonia to diacyl peroxide (VI) is between about the stoichiometric ratio and a 10-fold excess.

* * * * *

UNITED STATES PATENT AND TRADEMARK OFFICE
CERTIFICATE OF CORRECTION

PATENT NO. : 3,951,964
DATED : April 20, 1976
INVENTOR(S) : PIERRE TELLIER ET AL.

It is certified that error appears in the above-identified patent and that said Letters Patent are hereby corrected as shown below:

First page, ABSTRACT, second formula, right-hand moiety,

"$-N=C\diagup_{R^3}^{R^1}$" should read -- $-N=C\diagup_{R^3}^{R^1}$ --.

Column 1, line 13, "$\mathcal{CarbonNitrogen}$" should read -- $\mathcal{Carbon\text{-}Nitrogen}$ --.

Column 4, line 23, "tetrahydropyran2 -carboxaldehyde" should read -- tetrahydropyran-2-carboxaldehyde --.

Column 6, line 59, "alcaline" should read -- alkaline --.

Column 7, line 1, "salts of" should read -- salts by --.

Column 8, lines 37-41, the middle moiety of the formula should read --  --.

Column 10, line 32, "nonbornane2-" should read -- norbornane-2- --.

𝔖igned and 𝔖ealed this

Thirty-first 𝔇ay of August 1976

[SEAL]

Attest:

RUTH C. MASON
*Attesting Officer*

C. MARSHALL DANN
*Commissioner of Patents and Trademarks*